US00PP33788P2

(12) United States Plant Patent
Smit

(10) Patent No.: US PP33,788 P2
(45) Date of Patent: Dec. 28, 2021

(54) ***TRADESCANTIA* PLANT NAMED 'EC-TRADE-2011'**

(50) Latin Name: *Tradescantia cerinthoides*
Varietal Denomination: EC-TRADE-2011

(71) Applicant: EDEN COLLECTION B.V., Sappemeer (NL)

(72) Inventor: Obed Jacob Smit, Sappemeer (NL)

(73) Assignee: EDEN COLLECTION B.V., Sappemeer (NL)

( * ) Notice: Subject to any disclaimer, the term of this patent is extended or adjusted under 35 U.S.C. 154(b) by 0 days.

(21) Appl. No.: 17/331,297

(22) Filed: May 26, 2021

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Tradescantia* plant named 'EC-TRADE-2011', characterized by its uniform, compact and upright to broadly spreading plant habit; freely branching habit; dense and bushy appearance; strong and healthy leaves; green-colored leaves with light purple-colored longitudinal stripes; and good postproduction and interiorscape performance.

2 Drawing Sheets

Figure 1:
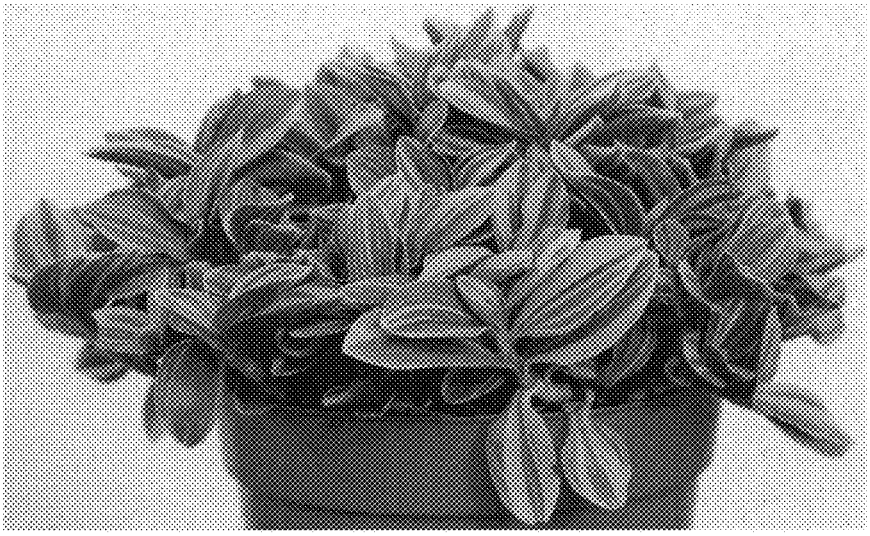

Botanical designation: *Tradescantia cerinthoides*.
Cultivar denomination: 'EC-TRADE-2011'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Eden Collection B.V. of Sappemeer, The Netherlands on Sep. 4, 2020, application number 2020/2115. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Tradescantia* plant, botanically known as *Tradescantia cerinthoides* and hereinafter referred to by the name 'EC-TRADE-2011'.

The new *Tradescantia* plant is a product of a planned breeding program conducted by the Inventor in Sappemeer, The Netherlands. The objective of the breeding program was to create new compact *Tradescantia* plants with attractive and unique leaf coloration and good overall plant performance.

The new *Tradescantia* plant is a naturally-occurring branch mutation of an unnamed selection of *Tradescantia*

*cerinthoides*, not patented. The new *Tradescantia* plant was discovered and selected by the Inventor on a single plant from within a population of plants of the patent selection in a controlled greenhouse environment in Sappemeer, The Netherlands in March, 2019.

Asexual reproduction of the new *Tradescantia* plant by terminal cuttings in a controlled greenhouse environment in Sappemeer, The Netherlands since April, 2019 has shown that the unique features of this new *Tradescantia* plant are stable and reproduced true to type in successive generations.

SUMMARY OF THE INVENTION

Plants of the new *Tradescantia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'EC-TRADE-2011'. These characteristics in combination distinguish 'EC-TRADE-2011' as a new and distinct *Tradescantia* plant:

1. Uniform, compact and upright to broadly spreading plant habit.
2. Freely branching habit; dense and bushy appearance.
3. Strong and healthy leaves.
4. Green-colored leaves with light purple-colored longitudinal stripes.
5. Good postproduction and interiorscape performance.

Plants of the new *Tradescantia* and the parent selection differ primarily in leaf color as plants of the parent selection have solid green-colored leaves without light purple-colored stripes.

Plants of the new *Tradescantia* can also be compared to plants of the *Tradescantia albiflora* 'Nanouk', disclosed in U.S. Plant Pat. No. 29,711. In side-by-side comparisons, plants of the new *Tradescantia* and 'Nanouk' differ primarily in the following characteristics:

1. Plants of the new *Tradescantia* are more compact than plants of 'Nanouk'.
2. Plants of the new *Tradescantia* have thinner stems than plants of 'Nanouk'.
3. Leaves of plants of the new *Tradescantia* are smaller than leaves of plants of 'Nanouk'.
4. Leaves of plants of the new *Tradescantia* are green in color with longitudinal light purple-colored stripes whereas leaves of plants of 'Nanouk' are green and greyed green in color with light purple-colored longitudinal stripes.

Plants of the new *Tradescantia* can also be compared to plants of the *Tradescantia spathacea* 'Tricolor', not patented. In side-by-side comparisons, plants of the new *Tradescantia* and 'Tricolor' differ primarily in the following characteristics:

1. Plants of the new *Tradescantia* are more compact than plants of 'Tricolor'.
2. Plants of the new *Tradescantia* are more freely branching than plants of 'Tricolor'.
3. Leaves of plants of the new *Tradescantia* are smaller and broader than leaves of plants of 'Tricolor'.
4. Leaves of plants of the new *Tradescantia* are green in color with longitudinal light purple-colored stripes whereas leaves of plants of 'Tricolor' are green and greyed green in color with light purple-colored longitudinal stripes.

BRIEF DESCRIPTION OF THE PHOTOGRAPHS

The accompanying colored photographs illustrate the overall appearance of the new *Tradescantia* plant showing the colors as true as it is reasonably possible to obtain in colored reproductions of this type. Colors in the photographs may differ slightly from the color values cited in the detailed botanical description which accurately describe the colors of the new *Tradescantia* plant.

The photograph on the first sheet (FIG. 1) comprises a side perspective view of a typical plant of 'EC-TRADE-2011' grown in a container.

Figure 2:
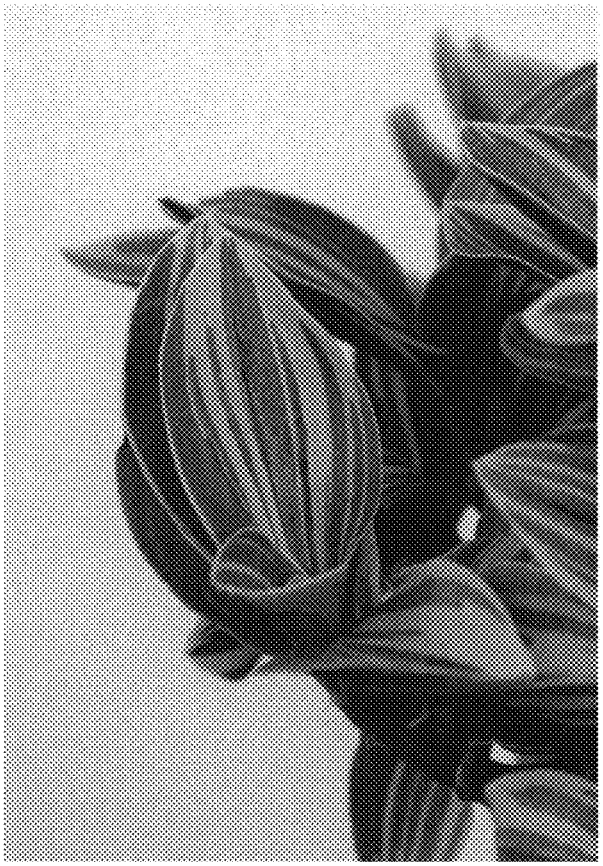

The photograph on the second sheet (FIG. 2) is a close-up view of typical leaves of 'EC-TRADE-2011'.

DETAILED BOTANICAL DESCRIPTION

The aforementioned photographs and following observations, measurements and values describe plants grown in 14-cm containers during the summer in a glass-covered greenhouse in Sappemeer, The Netherlands and under cultural practices typical of commercial *Tradescantia* production. During the production of the plants, day temperatures ranged from 18° C. to 21° C. and night temperatures ranged from 16° C. to 20° C. Plants were two months old when the photographs and description were taken. In the following description, color references are made to The Royal Horticultural Society Colour Chart, 2015 Edition, except where general terms of ordinary dictionary significance are used.

Botanical classification: *Tradescantia cerinthoides* 'EC-TRADE-2011'.

Parentage: Naturally-occurring branch mutation of an unnamed selection of *Tradescantia cerinthoides*, not patented.

Propagation:

*Type*.—By terminal cuttings; cuttings are propagated directly in the growing containers.

*Time to initiate roots, summer*.—About ten days at temperatures about 18° C.

*Time to initiate roots, winter*.—About two weeks at temperatures about 18° C.

*Root description*.—Typically white in color, actual color of the roots is dependent on substrate composition, water quality, fertilizers, substrate temperature and age of roots.

*Rooting habit*.—Freely branching; dense.

Plant description:

*Plant form and growth habit*.—Herbaceous perennial; uniform, compact and upright to broadly spreading plant habit; flattened globular in overall shape; moderately vigorous growth habit and low to moderate growth rate; good interiorscape performance with plants maintaining good quality for one to two years.

*Plant height*.—About 10.3 cm.

*Plant width* (*spread*).—About 23.6 cm.

*Lateral branches*.—Quantity: Freely branching habit with about 28 primary branches and about 84 secondary branches developing per plant. Length, primary branches: About 5.7 cm. Diameter, primary branches: About 3 mm. Internode length, primary branches: About 9 mm. Strength: Moderately strong. Aspect: Variable, from vertical to horizontal. Texture and luster: Smooth, glabrous; glossy. Color, developing: Close to 197A. Color, developed: Close to 148A; at the internodes, close to between 152A and 197A; with subsequent development, stems become closer to 197A to 197B.

Leaf description:

*Arrangement and quantity*.—Distichous; leaves simple and sessile; about seven leaves per branch.

*Length* (*excluding sheath*).—About 4.7 cm.

*Width*.—About 2.3 cm.

*Shape*.—Elliptic.

*Apex*.—Acute.

*Base*.—Oblique, sheathing.

*Margin*.—Entire.

*Aspect*.—Moderately concave.

*Texture and luster, upper surface*.—Smooth, glabrous; moderately velvety; slightly glossy.

*Texture and luster, lower surface*.—Smooth, glabrous; moderately glossy.

*Venation pattern*.—Parallel.

*Sheath length*.—About 7 mm.

*Sheath width*.—About 3 mm.

*Sheath texture*.—Densely pubescent.

*Sheath color*.—Close to 76D; venation, close to N77B.

*Color*.—Developing leaves, upper surface: Close to NN137C; towards the base, close to 146B and 146C; variable stripes, close to 75A and towards the base, stripes are closer to 75B. Developing leaves, lower surface: Close to 147A; variable stripes, close to 77B and towards the base, stripes are closer to 77C and 77D. Fully expanded leaves, upper surface: Close to 137A and NN137C; variable stripes, close to 77C; venation, similar to lamina colors. Fully expanded leaves, lower surface: Close to 79B and 79C; variable stripes, close to 77B; main vein, close to 146A and lateral venation, similar to lamina colors.

Flower description: To date, flower initiation and development have not been observed on plants of the new *Tradescantia*.

*Seeds and fruits*.—To date, seed and fruit development have not been observed on plants of the new *Tradescantia*.

Pathogen & pest resistance: Plants of the new *Tradescantia* have not been noted to be resistant to pathogens and pests common to *Tradescantia* plants.

Temperature performance: Plants of the new *Tradescantia* have been observed to tolerate temperatures ranging from 12° C. to 35° C. and to be suitable for USDA Hardiness Zones 10 to 12.

It is claimed:

1. A new and distinct *Tradescantia* plant named 'EC-TRADE-2011' as illustrated and described.

* * * * *